United States Patent
Harder

(10) Patent No.: US 11,311,710 B2
(45) Date of Patent: *Apr. 26, 2022

(54) CHEST VALVE FOR TREATING PNEUMOTHORAX

(71) Applicant: Robert Harder, Danville, VA (US)

(72) Inventor: Robert Harder, Danville, VA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/484,836

(22) Filed: Sep. 24, 2021

(65) Prior Publication Data

US 2022/0008712 A1    Jan. 13, 2022

Related U.S. Application Data

(63) Continuation of application No. 16/863,644, filed on Apr. 30, 2020.

(51) Int. Cl.
*A61M 39/24* (2006.01)
*A61M 39/02* (2006.01)
(Continued)

(52) U.S. Cl.
CPC .............. *A61M 39/24* (2013.01); *A61M 1/04* (2013.01); *A61M 39/0247* (2013.01); *A61M 2039/0276* (2013.01); *A61M 2205/02* (2013.01); *A61M 2210/101* (2013.01); *B32B 37/0076* (2013.01); *B32B 38/0004* (2013.01); *B32B 38/10* (2013.01); *B32B 2309/10* (2013.01); *B32B 2309/105* (2013.01)

(58) Field of Classification Search
CPC ............ A61M 39/24; A61M 2039/246; A61M 2039/244; A61M 1/04; A61M 2210/10; F16K 7/17; F16K 15/023
See application file for complete search history.

(56) References Cited

U.S. PATENT DOCUMENTS

| 2,594,525 A | 4/1952 | Walden et al. |
| 3,463,159 A | 8/1969 | Heimlich |

(Continued)

FOREIGN PATENT DOCUMENTS

| CN | 104147647 | 11/2014 |
| WO | 2008074109 | 6/2008 |

OTHER PUBLICATIONS

EP Search Report for EP 21170033.1, which is a corresponding EPO application to this U.S. application, dated Sep. 21, 2021, 9 pages.

*Primary Examiner* — Nathan R Price
*Assistant Examiner* — Melissa A Snyder
(74) *Attorney, Agent, or Firm* — Nixon & Vanderhye P.C.

(57) ABSTRACT

A chest valve including: a housing including an inlet configured to connect to a chest tube, an outlet and a fluid passage from the inlet to the outlet; and a one-way valve within the housing and included in the flow passage, wherein the one-way valve includes: (i) a first tubular strip wherein having an internal air passage and a first layer defining the air passage, wherein the first layer has a first thickness and the internal air passage of the first tubular strip is included in fluid passage of the housing; and (ii) a second tubular strip wherein having a second layer with a second thickness with a second thickness greater than the first thickness, wherein an outer surface of the second tubular strip is adjacent and overlaps an outer surface of the first tubular strip.

16 Claims, 3 Drawing Sheets

(51) Int. Cl.
*A61M 1/04* (2006.01)
*B32B 37/00* (2006.01)
*B32B 38/00* (2006.01)
*B32B 38/10* (2006.01)

(56) References Cited

U.S. PATENT DOCUMENTS

| | | |
|---|---|---|
| 3,651,810 A | 3/1972 | Ormerod |
| 3,734,154 A * | 5/1973 | Polk ................ B65D 33/30 383/57 |
| 3,967,645 A | 7/1976 | Gregory |
| 4,289,166 A | 9/1981 | Haines |
| 4,966,197 A | 10/1990 | Jaron et al. |
| 5,263,922 A | 11/1993 | Sova et al. |
| 5,327,871 A | 7/1994 | Gryc |
| 7,406,963 B2 | 8/2008 | Chang et al. |
| 7,445,028 B1 * | 11/2008 | Aanonsen ............ F16K 15/147 137/849 |
| 7,533,696 B2 * | 5/2009 | Paul, Jr. .............. F16K 15/147 137/846 |
| 7,533,969 B2 | 5/2009 | Ozaki et al. |
| 8,518,053 B2 | 8/2013 | Tanaka et al. |
| 2006/0229586 A1 | 10/2006 | Faries |
| 2007/0027433 A1 | 2/2007 | Garcia et al. |
| 2008/0289696 A1 | 11/2008 | Bushman |
| 2021/0338996 A1 * | 11/2021 | Harder ............ A61M 39/0247 |

* cited by examiner

CHEST VALVE FOR TREATING PNEUMOTHORAX

RELATED APPLICATION

This application is a continuation of and incorporates by reference U.S. patent application Ser. No. 16/863,644, filed Apr. 30, 2020.

TECHNICAL FIELD

The present invention relates to chest valves, also known as flutter valves, used in medical devices to treat a pneumothorax.

BACKGROUND

A chest valve, also known as a Heimlich valve, is a one-way valve used to release air and other fluids from a pneumothorax, while preventing air flow into the pleural space between the lung and chest wall. A pneumothorax is a collapsed lung and is typically caused by excess air in the pleural space that compresses the lung. A chest valve is used to treat a pneumothorax by releasing the excess air from the plural space and allowing the lung to properly inflate.

A typical chest valve includes a one-way valve flutter valve, e.g., duck-bill valve, housed in a casing connected to a drainage tube inserted through the chest wall of a patient. Examples of chest valves are disclosed in U.S. Pat. Nos. 3,463,159 and 7,533,696.

To prevent air from entering the pleural cavity through the chest valve, the valve must fully close when the outside air pressure is greater than the pressure in the pleural cavity. Air leaking through the valve can enter the pleural cavity and exasperate pneumothorax. There is a long felt need for chest valves that completely close and prevent air leaking through the valve and into the pleural cavity.

SUMMARY OF INVENTION

An inventive chest valve is disclosed herein which may include a one-way flutter valve formed of a first strip of thin lay-flat polyethylene tubing. An inlet end of the first strip is attached to an airflow port in the housing of the chest valve. The outlet end of the first strip need not be attached directly to the housing. The outlet of the first strip is closed, e.g., lies flat, except while fluid flows into the inlet and from the outlet of the first strip. A second strip of thicker lay-flat polyethylene tubing is fused to the first strip along a common longitudinal edge of the strips. The opposite longitudinal sides of the strips is formed by longitudinal folds in both strips. The second strip assists in closing the first strip except while fluid flows from the inlet to the outlet of the first strip.

In one embodiment, the invention is a chest valve including: a housing including an inlet configured to connect to a chest tube, an outlet and a fluid passage from the inlet to the outlet; and a one-way valve within the housing and included in the flow passage, wherein the one-way valve includes: (i) a first tubular strip wherein having an internal air passage and a first layer defining the air passage, wherein the first layer has a first thickness and the internal air passage of the first tubular strip is included in fluid passage of the housing; and (ii) a second tubular strip wherein having a second layer with a second thickness with a second thickness greater than the first thickness, wherein an outer surface of the second tubular strip is adjacent and overlaps an outer surface of the first tubular strip.

The invention may also be embodied as a one-way valve comprising: a first tubular strip wherein having an internal air passage and a first layer defining the air passage, wherein the first layer has a first thickness and the internal air passage of the first tubular strip is included in fluid passage of the housing; and a second tubular strip wherein having a second layer with a second thickness with a second thickness greater than the first thickness, wherein an outer surface of the second tubular strip is adjacent and overlaps an outer surface of the first tubular strip.

Further, the invention may be embodied as: a method to make a chest valve comprising: dispensing a first length of lay flat tubing from a first roll of lay flat tubing, wherein a layer forming the first length has a first thickness; dispensing a second length of lay flat tubing from a second roll of lay flat tubing, wherein a layer forming the second length has a second thickness greater than the first thickness; overlapping the first and second lengths of lay flat tubing, wherein folded edges align of the first and second lengths of lay flat tubing; fusing the first and second lengths of lay flat tubing to create a longitudinal heat seal line extending longitudinally along the first and second lengths; cutting the fused first and second strips of lay flat tubing into a first strip and a second strip, wherein the first and section strips are fused along the heat seal line; attaching an inlet end of the first strip to a port in the chest valve, and inserting the fused first and second strips into a housing of the chest valve. The method may further include trimming a section of the fused first and second lengths, wherein the section is between the heat seal line and an edge of the first and second lengths.

SUMMARY OF DRAWINGS

The invention can be better understood with reference to the aforementioned and following drawings and description. In the drawings.

DETAILED DESCRIPTION

Figure 1:
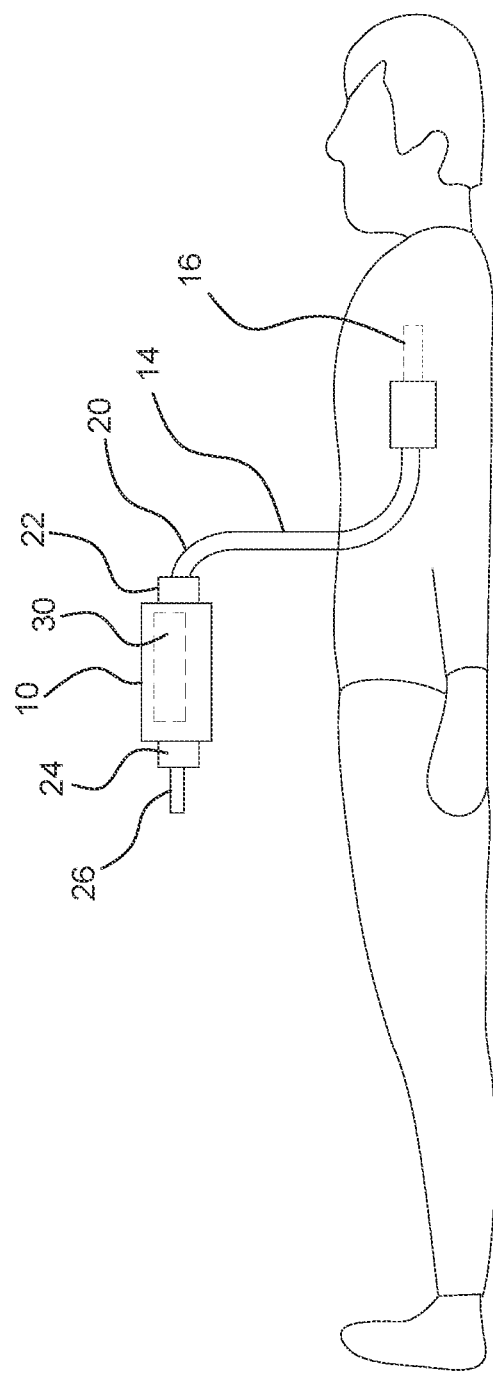
FIG. 1 is a schematic diagram of a chest valve on a patient with a pneumothorax.

FIG. 1 illustrates a chest valve 10 attached to the chest of a patient 12. A chest tube 14 includes a distal end 16 inserted into the pleural cavity through the chest wall. A suture, gauze and/or compress or other medical device 18 may be applied to the skin to secure the chest tube to the patient. A proximal end 20 of the chest tube is attached to an inlet 22 of the chest valve 10. An outlet 24 of the chest valve is a port connected to a discharge tube 26 which may lead to a collection bag.

Air, blood and other fluids flow from the pleural cavity through the chest tube 14, the chest valve 10 and out the discharge tube 26. Air does not flow in the other direction. The chest valve 10 prevents reverse air flow in which air flows through the chest valve, the chest tube 14 and into the pleural cavity. The reverse air flow is prevented by a one-way valve 30 in the chest valve.

The one-way valve 30 allows air to flow only from the inlet 22 to the outlet 24 of the chest valve. The one-way valve 30 may be a flutter valve, e.g., a duckbill valve, having an inlet which is continuously held open and an outlet that is closed except when fluid pressure at the inlet is sufficient to force open the outlet end of the valve. The inlet 22 and outlet 24 may each include a tapered port with an internal air passage and outer surfaces with ribs to assist in coupling to the chest tube and discharge tube.

Figure 2:
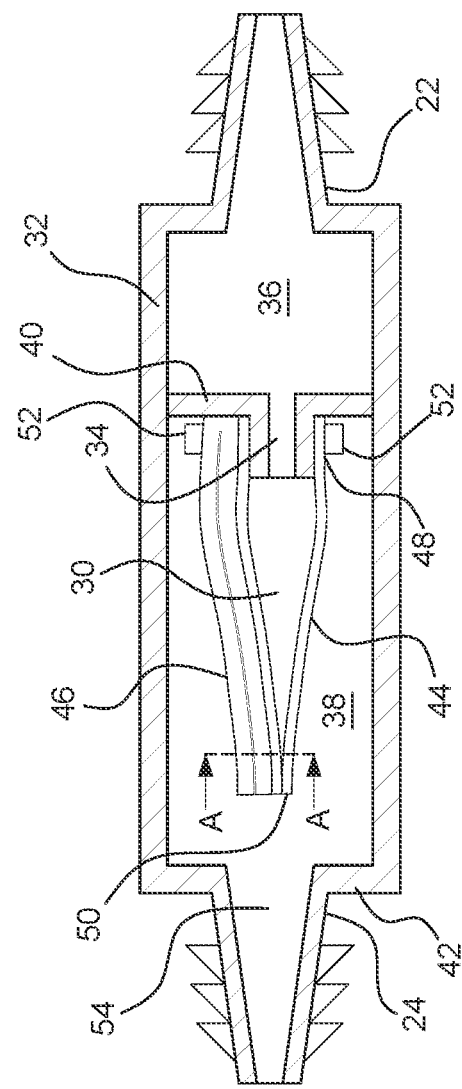
FIG. 2 is a cross-sectional view of a chest valve.

FIG. 2 shows the chest valve 10 in cross section. A one-way valve 30 is housed within a cylindrical housing 32 of the chest valve. At one end of the housing 32 is a cylindrical inlet housing 34 that includes at one end the inlet 22 and at an opposite end a cylindrical port 34 within the cylindrical housing 32. A chamber 36 in the inlet housing 34 allows air flowing through the inlet 22 to pass through to the port 34.

The one-way valve 30 is in an enclosed chamber 38 within the cylindrical housing 32. One end of the chamber 38 is closed by a proximal wall 40, e.g., a circular disc, that includes an opening aligned with the port 34. The other end of the chamber 38 is closed by a distal wall 42, e.g., a circular disc, that includes an opening aligned with the outlet 24.

The one-way valve 30 is an assembly of two strips 44, 46 of lay-flat polyethylene tubing. The first strip 44 is tubing of a thin layer of polyethylene, such as a layer 2 mils (0.051 mm) thick, and the second strip 46 is tubing of a thick layer of polyethylene, such as a layer at least 4 mils (0.100 mm) thick.

The first strip 44 forms the valve portion of the one-way valve 30. An inlet end 48 of the first strip is attached to the port 34 within the chest valve 10 and always remains open. The inlet end 48 is secured to an outer surface of the port 34 by an adhesive or a clip 52. The first strip 44 extends into the chamber 38. The first strip 44 and the second strip 46 are supported in the chamber 38 solely by the attachment of the first strip 44 to the port.

The first and second strips 44, 46 are flexible and may move within the chamber 38. The widths and lengths of the first and section strips 44, 48 may be substantially the same. The width of the strips may be slightly narrower than the internal diameter of the chamber 38 so that the strips substantially span the diameter of the interior of the chamber 38. For example, the width of the strips 44, 46 may be in a range of 95% to 75%, or 90% to 80%, of the internal diameter of the chamber.

The outlet end 50 of the first strip 44 faces and proximate to an opening 54 in the distal wall 42 of the chamber 38. The outlet end 50 of the first strip is normally flat and closed within the chest valve. The outlet end of the first strip opens to allow fluid to flow through the strip when fluid enters the inlet end of the first strip.

The second strip 46 of the one-way valve 30 overlaps the first strip 44 along, for example, the entire length of the first strip. The width and length of the second strip may be the same as the first strip. The first and second strips may be formed of the same material, such as lay flat polyethylene tubing. The difference between the first and second strips may be limited to the thickness of the polyethylene layer used to form the tubing. The thickness of the layer forming the first strip 44 is less than the thickness of the layer forming the second strip. For example, the thickness of the layer forming the first strip may be one-third to two-thirds the thickness of the layer that forms the second strip.

Figure 3:
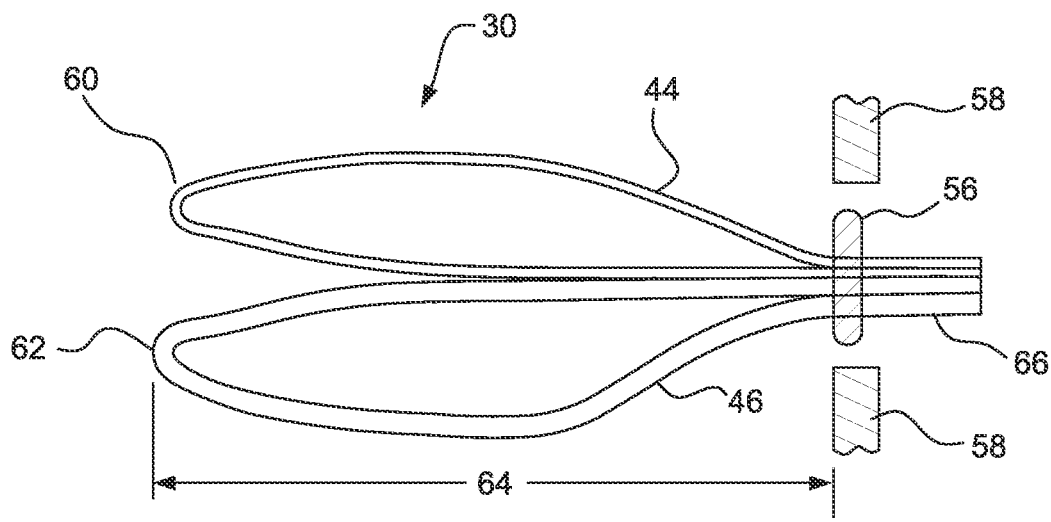
FIG. 3 is a cross-sectional view of two tubular strips of lay flat tubing, wherein the cross section is along a line perpendicular to the longitudinal axis of the strips.

As shown in FIG. 3, the one-way valve 30 may be formed from folded tubes, e.g., lay-flat polyethylene tubes, that are heat sealed together along a longitudinal heat seal line 56 extending the length of the strips. A heating element 58, such as one roller or a pair of opposing rollers, applies heat to the first and section strips 44, 46 to fuse together the polyethylene layers forming the strips. The heat seal line 56 forms a longitudinal edge of the one-way valve 30.

Figure 4:
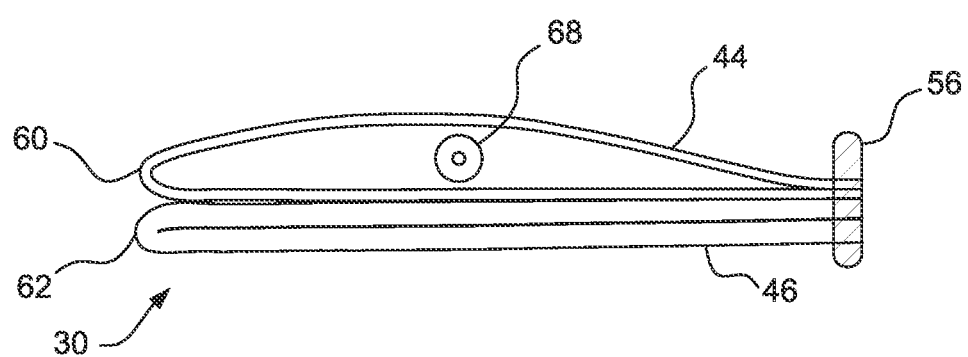
FIG. 4 is a cross-sectional view of the one-way valve shown in FIG. 2, wherein the cross section is taken along line A-A in FIG. 2 and the first strip is open.
Figure 5:
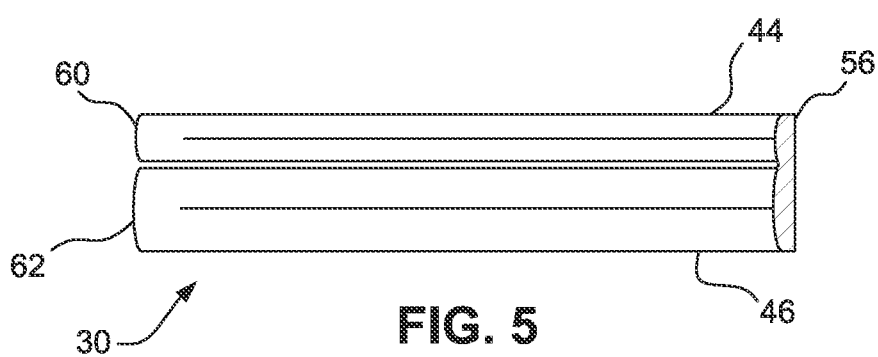
FIG. 5 is a cross-sectional view of the one-way valve shown in FIG. 2, wherein the cross section is taken along line A-A in FIG. 2 and the first strip is closed.

A second longitudinal edge of the valve 30 is formed by the folded edges 60, 62 of the first and second strips 44. The folded edges 60, 62 are aligned and overlap, such as shown in FIGS. 4 and 5. The width 64 of the one way valve 30 is the distance between the heat seal line 56 and the folded edges 60, 62.

The second strip 46 is attached to the first strip 44 solely along the heat seal line. The second strip 46 need not be attached to the port 34. The ends of the second strip need not be attached to the chest valve 10.

The dimensions of the one-way valve 30 may be a length of four to six inches, and a width from one-half an inch to an inch. The length and width of the one-way valve may be selected to fit inside the cylindrical housing 32. The length and width of the first and second strips 44, 46 may be substantially the same, such that the length and width of the first strip differs by no more than five to ten percent of the length and width of the second strip.

FIGS. 4 and 5 show the one-way valve 30 in cross-section along line A-A in FIG. 2. FIG. 4 shows the first strip 44 in an open position and FIG. 5 shows the first strip in a closed position.

The second strip tends to lay flat against one side of the first strip 44, such that the fold lines 60, 62 of the strips are aligned and overlap. The greater thickness of the layers forming the second strip 46 assists in flattening the first strip 44, as is shown in FIG. 5. The purpose of the second strip is to assist the first strip to lay flat when no air is flowing through the first strip.

A test of a one-way valve 30 with first and second strips demonstrated that the first strip 44 tended to lay flat, as shown in FIG. 5, when joined to the second strip 46 by the heat seal line 56 to a greater extent than when the first strip was alone and without the second strip.

The reasons are not entirely understood as to why attaching a second strip assists in making the first strip lay flat and stay closed. The reasons may include that the second strip is thicker and thus tends to lie flat to a greater extend than the thinner first strip, and that as the second strip lies flat it pulls the first strip to a flat state. The first strip is thin and tends to twist, wrinkle and not fully close, especially along a fold line. The second strip is thick and thus stiffer than the first strip. The second strip is less likely to twist, wrinkle and not fully close, as compared to the first strip. The stiffness of the second strip may provide support for the first strip that causes the first strip to close, except when air flows from the inlet to the outlet of the first strip.

A benefit of having the first strip 44 entirely flat except when air flows from the inlet to the outlet, is that air cannot pass through the first strip while the strip is entirely flat. As can be seen in FIG. 5, there is no gap between the layers of the first strip 44 while the strip is closed and lying flat. To avoid gaps within the first strip, the first strip should lay flat except while air flows from the inlet to the outlet of the strip.

FIG. 4 shows the first strip 44 is an open position due to air flow 68 flowing through the air passage within the first strip. The air flows from the inlet 48 to the outlet 50 of the first strip. The pressure of the air flow causes the first strip to open to allow the airflow 68.

The location of the heat seal line 56 across the width of the first and second strips 44, 46 is selected so that the width 64 of the one-way valve corresponds to a desired width of the one-way valve 34. After the heat seal line 56 is formed, the portions of the strips 44, 46 extending beyond the desired width 64 is removed and discarded, such as by cutting or slicing the portion at or near the heat seal line 56.

FIG. 5 shows the first and second strips 44, 46 flat such that the air passage through the first strip is closed. In particular, the corner of the air passage near the folded edge 60 is closed such that no air leaks through the corner.

Figure 6:
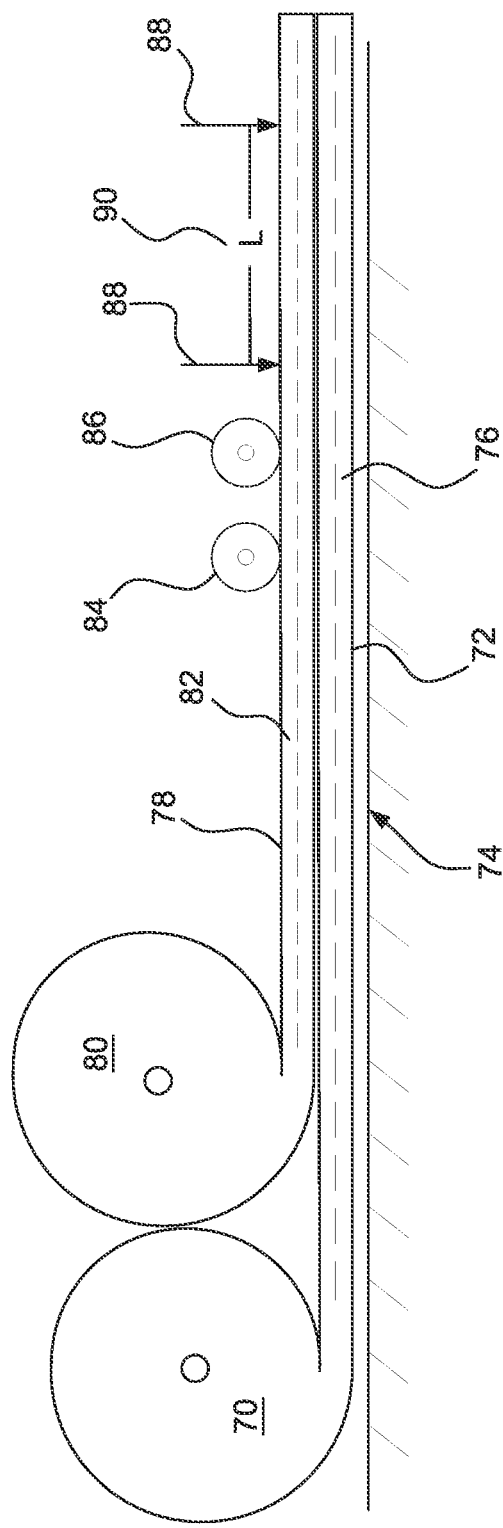
FIG. 6 is a schematic diagram showing the manufacture of the one-way valve.

As shown in FIG. 6, the one-way valve 30 may be formed using a first roll 70 of lay flat polyethylene by dispensing a first length 72 of lay flat tubing from the first roll 70 on a table 74 or other working surface. The lay flat tubing of the first roll 70 is formed of a layer 76 arranged in a tube with folded side edges. The layer 76 may be polyethylene with a first thickness, such as in a range of 3 to 6 mils, or 4 mils.

A second length 78 of lay flat tubing from a second roll 80 of lay flat tubing is unrolled to overlap the first length 72. The second roll is formed of a layer 82 arranged in a tube with folded side edges. The layer 82 may be polyethylene with a second thickness in a range of 1 mil to 3 mil, or 2 mils. The second thickness may be in a range of one-third to two-thirds, such as one-half, the thickness of the first layer.

The second length 78 is arranged to overlap the first length 72 such that the folded edges are aligned of the first and second lengths.

A heating element 84, such as a heated roller(s), is applied to the overlapping lengths 72, 78 to fuse the lengths along a longitudinal heat seal line 56. A cutting roller 86 may be used to slice the fused lengths along a longitudinal line that is adjacent the heat seal line, and between the heat seal line and one of the folds in the lengths of lay flat tubing. The remaining portion of the fused lengths 72, 78 overlap and have a common width 64 that is selected to fit into a housing 32 of a chest valve.

The fused lengths 72, 78, after removal of the portion cut by the cutting roller 86, is cut using a knife(s) 88 along lateral lines. The resulting strips 90 of fused lay-flat tubing are used to form one-way valves 30, by attaching an inlet end of the thinner lay-flat tube in a strip 90 to a port 34 in the housing 32 of the chest valve 10.

Advantages of the manufacturing method of the one-way valve 30 include ease of manufacture and low cost of materials and manufacture. The materials may be rolls of strips of lay flat polyethylene tubing are common, commercially available products. These rolls are available with layers of different thicknesses, such as 2 mil and 4 mil layers. Devices for heat sealing polyethylene layers and cutting the layers are inexpensive and easy to use. Another advantage is that the polyethylene material does not cause allergic reactions in some people as does latex material used in some conventional valves.

While at least one exemplary embodiment of the present invention(s) is disclosed herein, it should be understood that modifications, substitutions and alternatives may be apparent to one of ordinary skill in the art and can be made without departing from the scope of this disclosure. This disclosure is intended to cover any adaptations or variations of the exemplary embodiment(s). In addition, in this disclosure, the terms "comprise" or "comprising" do not exclude other elements or steps, the terms "a" or "one" do not exclude a plural number, and the term "or" means either or both. Furthermore, characteristics or steps which have been described may also be used in combination with other characteristics or steps and in any order unless the disclosure or context suggests otherwise.

The invention claimed is:

1. A chest valve comprising:
a housing including an inlet configured to connect to a chest tube, an outlet and a flow passage from the inlet to the outlet; and
a one-way valve within the housing and included in the flow passage, wherein the one-way valve includes:
a first tubular strip formed of a first flexible layer which defines an internal fluid passage, wherein the first flexible layer has a first thickness, and the internal fluid passage of the first tubular strip is included in flow passage of the housing; and
a second tubular strip formed of a second flexible layer with a second thickness greater than the first thickness, wherein an outer surface of the second tubular strip is adjacent and overlaps an outer surface of the first tubular strip,
wherein the second tubular strip is fused to the first tubular strip along a heat seal line extending longitudinally along first longitudinal edges of the first and second tubular strips, and the first and second tubular strips include second longitudinal edges opposite to the first longitudinal edges.

2. The chest valve of claim 1, wherein an inlet end of the first tubular strip is attached to a port in the housing, and the port is in the flow passage.

3. The chest valve of claim 1, wherein the first tubular strip has a width and length no greater than a width and length of the second tubular strip.

4. The chest valve of claim 1, wherein a width and length of the first tubular strip equals a width and length of the second tubular strip.

5. The chest valve of claim 4, wherein the second longitudinal edges are longitudinal folds in the first flexible layer and the second flexible layer.

6. The chest valve of claim 1, wherein the first tubular strip and the second tubular strip are formed of polyethylene stay flat tubing.

7. The chest valve of claim 6, wherein the first thickness is 2 mil and the second thickness is 4 mil.

8. The chest valve of claim 1, wherein the first thickness is in a range of one-third to two-thirds the second thickness.

9. A one-way valve comprising:
a housing including a flow passage extending through the housing;
a first tubular strip formed of a first flexible layer defining an internal fluid passage, wherein the first flexible layer has a first thickness and the internal fluid passage is included in the flow passage extending through the housing; and
a second tubular strip formed of a second layer having a second thickness greater than the first thickness,
wherein an outer surface of the second tubular strip is adjacent and overlaps an outer surface of the first tubular strip, and
wherein the second tubular strip is fused to the first tubular strip along a heat seal line extending longitudinally along the first and second tubular strips.

10. The one-way valve of claim 9, wherein the heat seal line is at first longitudinal edges of the first and second tubular strips, and the first and second tubular strips include second longitudinal edges opposite to the first longitudinal edges.

11. The one-way valve of claim 10, wherein the second longitudinal edges are longitudinal folds in the first flexible layer and the second flexible layer.

12. The one-way valve of claim 9, wherein the first tubular strip and the second tubular strip are formed of polyethylene stay flat tubing.

13. The one-way-valve of claim 9, wherein the first thickness is in a range of one-third to two-thirds the second thickness.

14. The one-way valve of claim 9, wherein the first tubular strip has a width and length no greater than a width and length of the second tubular strip.

15. The chest valve of claim 2, wherein the second tubular strip does not define an internal passage connected to the port in the housing.

16. The one-way valve of claim 9, wherein an inlet end of the first tubular strip is attached to a port in the housing, and the port is in the fluid flow passage, and wherein the second tubular strip does not define an internal passage connected to the port in the housing.

* * * * *